United States Patent [19]
Tritsch

[11] 3,930,502
[45] Jan. 6, 1976

[54] DISPOSABLE DIAPER WITH A TAPE CLOSURE SYSTEM HAVING A DOUBLE-FOLDED TAB

[75] Inventor: Ludwig Tritsch, Wilmette, Ill.

[73] Assignee: Johnson & Johnson, New Brunswick, N.J.

[22] Filed: Nov. 20, 1974

[21] Appl. No.: 525,424

[52] U.S. Cl. .................. 128/287; 128/284; 24/67
[51] Int. Cl.² ......................................... A61F 13/16
[58] Field of Search ........ 128/284, 287, 290 R, 286; 24/67

[56] References Cited
UNITED STATES PATENTS

| | | |
|---|---|---|
| 3,646,937 | 3/1972 | Gellert .............................. 128/287 |
| 3,810,472 | 5/1974 | Aldinger ............................ 128/287 |
| 3,840,013 | 10/1974 | Mesek ................................ 128/287 |
| 3,848,594 | 11/1974 | Buell .................................. 128/284 |
| 3,875,621 | 4/1975 | Karami ................................ 24/67 |

Primary Examiner—Aldrich F. Medbery

[57] ABSTRACT

A disposable diaper is provided with an improved adhesive tab having a relatively long free end. The tab comprises a fixed end secured to a diaper backing sheet on the outside surface of the diaper and at a marginal location thereof, and a free end having a tacky surface covered with a release strip which extends beyond the tacky surface. The release strip and the free end together form a creasable laminate which is folded back over the fixed tab end and further folded over on itself.

3 Claims, 4 Drawing Figures

U.S. Patent  Jan. 6, 1976  3,930,502
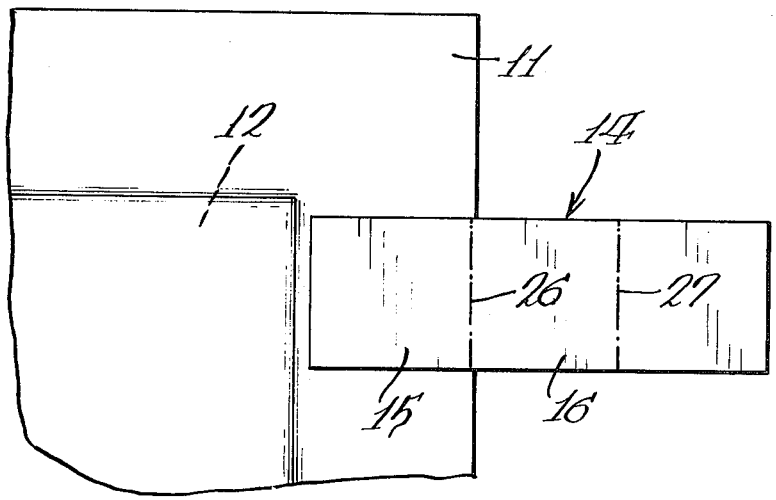
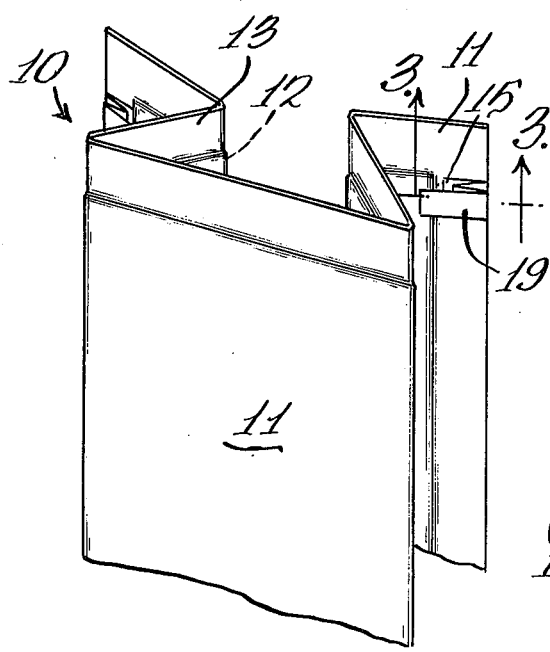
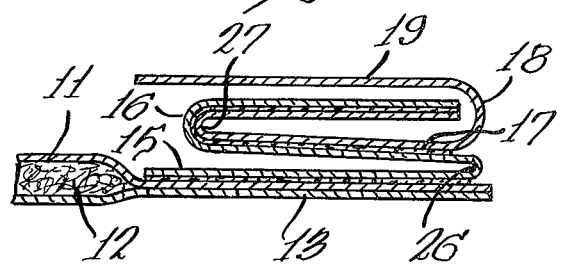
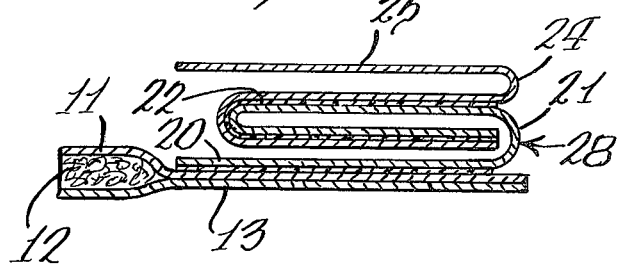

DISPOSABLE DIAPER WITH A TAPE CLOSURE SYSTEM HAVING A DOUBLE-FOLDED TAB

BACKGROUND OF THE INVENTION

This invention relates to disposable diapers. More particularly, this invention relates to disposable diapers adapted to be secured in place by adhesive tabs.

Disposable diapers provide substantial advantages in convenience over conventional diapers and commonly have a generally quadrilateral configuration with straight or curvilinear longitudinal edges. Disposable diapers are conveniently secured about an infant by means of adhesive tape tabs which are affixed to the diaper along a longitudinal edge thereof, thus eliminating the need for extraneous fasteners, such as pins. In order to protect the adhesive surfaces of the tape tabs, usually a release sheet is applied over these adhesive surfaces for subsequent removal when the diaper is about to be used. However, such tabs usually project beyond the confines of the diaper to a considerable extent and interfere with the efficient manufacture and packaging of the diaper.

In an attempt to solve the foregoing problems, U.S. Pat. No. 3,776,234 to Hoey proposes to fold the tab over on itself at the diaper's edge and to adhesively attach a portion of the folded-over tab segment to the inside surface of the diaper in order to keep the tab from interfering with the manufacturing machinery and with the folding and packaging operations. This requires that the edge of the diaper backing sheet be folded over to present an attachment surface at the front or inside face of the diaper and a relatively involved tab design is necessary for this purpose. Also, undesirable tearing of the diaper facing fabric may result if such a tab is adhesively attached to the facing fabric of the diaper.

U.S. Pat. No. 3,646,937 to Gellert shows a fastening tab which is provided with a release surface which is permanently bonded to the inside surface of the diaper; however, such an arrangement is disadvantageous because the release surface may be placed in contact with the infant's skin when the diaper is used.

Additionally, for ease of application of the diaper about an infant, a relatively long free end for the adhesive pad is desirable, yet the longer the free end the more severe are the manufacturing and packaging problems.

SUMMARY OF THE INVENTION

The present invention contemplates a disposable diaper provided with an improved adhesive tab fastener having a relatively longer free end. The disposable diaper embodying the present invention comprises a thin, moisture-impervious backing sheet, a moisture-retaining layer which includes a pad of absorbent material superposed on the backing sheet and attached thereto, and an adhesive tab having a fixed end secured to the backing sheet on the outside surface of the diaper and at a marginal location thereof and a free end longer than the fixed end and provided with a tacky surface which faces in the same direction as the inside surface of the diaper. A cover strip provided with a release coating on one surface thereof is releasably attached to and covers the tacky surface. Moreover, the cover strip extends longitudinally beyond the tacky surface, and the free end together with the cover strip forms a creasable laminate which is folded back over the fixed end and further folded over on itself.

BRIEF DESCRIPTION OF THE DRAWING

In the drawing,

FIG. 1 is a fragmentary view of a disposable diaper showing an adhesive tab attached thereto;

FIG. 2 is a fragmentary perspective view of a diaper embodying the present invention;

FIG. 3 is a fragmentary elevational view, on an enlarged scale, taken along plane 3—3 in FIG. 2; and FIG. 4 is a fragmentary elevational view similar to that of FIG. 3 and showing a further embodiment of the present invention.

DESCRIPTION OF THE PREFERRED EMBODIMENTS

Referring to FIGS. 1 and 2, disposable diaper 10, having a substantially quadrilateral configuration is provided with moisture-impermeable backing sheet 11 which forms an outside surface for direction away from an infant and with an absorbent pad means 12 situated on backing sheet 11 and attached thereto. Moisture-pervious facing sheet 13, forming an inside surface for direction toward the infant, overlies absorbent pad 12 and is substantially coextensive with backing sheet 11. Adhesive tab 14 comprises fixed end 15 attached to the outer surface of backing sheet 11 at a marginal location of diaper 10 and free end 16 which extends beyond the longitudinal margin of diaper 10. Free end 16 is longer than attached or fixed end 15. Crease lines 26 and 27 traverse free end 16.

Referring to FIG. 3, free end 16 is provided with pressure-sensitive adhesive layer 17 which presents a tacky surface facing in the same direction as the diaper inside surface defined by facing sheet 13 when adhesive tab 14 is extended preparatory to use. Cover sheet 18 is provided with a suitable release coating and is releasably adhered to adhesive layer 17 carried by free end 16 and shielding adhesive layer 17. While the major portion of cover strip 18 is coextensive with free end 16, portion 19 of cover strip 18 extends longitudinally beyond the tacky surface provided by adhesive layer 17 and provides a convenient grip tab means for ultimately separating cover strip 18 from free tab end 16. The resulting laminate comprising free end 16 and cover strip 18 is then folded along crease lines 26 and 27 (FIG. 1) so that adhesive tab 14 assumes a S-configuration. Portion 19 of cover strip 18 projects outwardly from the produced S-fold and is folded back over the distal portion of free end 16. To produce the aforesaid S-fold, the laminate is initially folded back over fixed end 15 and thereafter folded over on itself.

Another embodiment is illustrated in FIG. 4. Adhesive tab 28 having fixed end 20 and free end 21 is provided with release-coated cover strip 24 which overlies pressure-sensitive adhesive layer 22 provided on free end 21. Adhesive layer 22 is again positioned on free end 21 so that a tacky surface is presented in the same direction as the diaper inside surface when tab 28 is extended. Cover strip 24 is provided with grippable portion 25 which extends beyond adhesive layer 22 and is folded back on itself. Adhesive tab 28 together with major portion of cover strip 24 is folded in a collapsed spiral configuration so that the distal portion of free end 21 is situated between the rest of free end 21 and fixed end 20. The attachment of fixed end 20 to backing sheet 11 can be effected by means of a further pressure sensitive adhesive layer provided on the surface thereof facing backing sheet 11, by heat-sealing or fusion in the case of thermoplastic materials, or in any other convenient manner.

The adhesive tab suitable for the purposes of the present invention can be made from a wide variety of materials, provided that such materials are sufficiently pliant to be creasable. Particularly preferred materials for this purpose are polyalkylene webs such as high density polyethylene sheet, polypropylene sheet, and the like, suitably modified with an appropriate filler if necessary. Adhesive-coated paper as well as woven or non-woven fabrics provided with an adhesive layer are also suitable materials for the adhesive tabs.

The pressure-sensitive adhesive layers such as layer 17 and layer 22 are provided by applying a coating of pressure-sensitive adhesive composition known in the art to the appropriate surfaces of respective free ends 16 and 21. The applied adhesive shall have good tack, good cohesive strength, good resistance to moisture and good resistance to aging. Illustrative of such adhesive compositions are mixtures of natural or synthetic rubber, zinc oxide, and various resins, also latices of natural or synthetic rubber, or water dispersions of acrylic tacky polymers or copolymers.

Cover strips 18 and 24 can be made from smooth plastic film having a relatively non-adhering surface, from paper coated with a silicone compound, or similar materials.

Several different types of facing materials may be used for diaper facing sheet 13. For example, facing sheet 13 may be made up of a mixture of fibers consisting predominantly of inexpensive short cellulosic fibers such as wood pulp fibers or cotton linters, in amounts of about 75 to about 98 percent, the balance being textile length fibers such as rayon as described in U.S. Pat. No. 3,663,348 to Liloia et al.

Facing sheet materials suitable for use in this invention can have fabric weights in the range of about 1 to 5 oz/yd$^2$ and densities of less than 0.15 g/cc, generally in the range between 0.05 and 0.1 g/cc. The dry strength of the facing sheet for a fabric having a weight of about 1.5 oz/yd$^2$ is at least 0.15 lbs/in of width in the machine direction and at least 0.1 lbs/in of width in the cross direction. Such fabrics have unusually good elongation, loft, softness, and drape characteristics in comparison to prior products incorporating any substantial amount of short fibers.

Facing sheet 13 may also be made of an apertured, non-woven fabric which is formed, for example, in accordance with the teachings of commonly assigned U.S. Pat. Nos. 2,862,251; 3,081,514; and 3,081,515. Briefly, such fabrics are foraminous structures wherein groups or groupings of fibers have been rearranged from a fibrous nonwoven starting web into positions surrounding less dense fabric portions by passage of a fluid through the starting material. The fibers within the groupings are mechanically interlocked, and may be arranged into various patterns, as is well known by those skilled in the art. A suitable binder may be utilized to help retain the fibers in their rearranged locations, as is also well known by those skilled in the art. The fabric can be made of naturally occurring fibers, synthetic fibers, or blends thereof. Typical facing sheets made of a polyester type material can have a weight of about 0.75 oz./yd.$^2$.

In addition, facing sheet 13 can be formed of a non-apertured material, such as a nonwoven isotropic web, or the like. In all of the aforementioned facing materials, the material should be relatively hydrophobic so as to retard wicking within the facing layer.

Highly moisture-absorbent fibrous pad or batt 12, which usually is substantially rectangular in shape but smaller than the facing sheet and the backing sheet, is centrally disposed between facing sheet 13 and backing sheet 11. Pad 12 is usually anchored to backing sheet 11 by means of an adhesive bead, heat sealing, or similar expedients. Pad 12 can be formed in accordance with the teachings of U.S. Pat. No. 3,612,055 to Mesek et al. If desired, a highly moisture-absorbent layer can be provided substantially coextensive with backing sheet 11 and facing sheet 13.

A suitable backing sheet material for the diapers embodying the present invention can be an opaque polyethylene web about 0.001 inch thick. Another suitable material for this purpose is a polyethylene terephthalate web having a thickness of about 0.0005 inch. Typical disposable diapers which can be fitted with tab-type adhesive fasteners described hereinabove are shown in U.S. Pat. No. 3,612,055 to Mesek et al. and in U.S. Pat. No. 3,683,916 to Mesek et al. Other suitable disposable diaper structures which can be improved by the present tab-type fasteners are shown in U.S. Pat. No. Re. 26,151 to Duncan et al.

In use, a diaper equipped with the adhesive fasteners of the present invention is applied to the infant by laying out the diaper on a suitable flat surface and placing the infant thereon so that the waist-underlying end of the diaper is that having the fastener means. The other end of the diaper then extends downwardly between the infant's legs. Next, the downwardly-extending end of the diaper is brought up between the infant's legs to a position contiguous with the front of the infant's waist. The diaper is thereafter secured to the infant by placing the corners of the waist portion of the abdomen-covering end as far around the infant's waist as they will go and by bringing the corners of the underlying end of the diaper into an overlapping relationship with the aforementioned corners so that the diaper snugly encircles the infant's waist and provides a custom fit. The adhesive fasteners are then prepared for use by grasping cover strip terminal portions such as portion 19 or portion 25 and pulling the cover strip away from the adhesive surface on the free end of the adhesive tab. The tabs are then used to secure the diaper in the desired position by simply urging the pressure-sensitive adhesive surfaces in contact with the adjacent outer surface of the diaper.

The foregoing description and the drawing are illustrative but are not to be taken as limiting. Still other variations and modifications are possible without departing from the spirit and scope of the present invention.

I claim:

1. In combination with a disposable diaper having an inside surface for direction toward an infant when the diaper is worn by that infant and an outside surface for direction away from said infant and provided with a moisture-retaining layer and a moisture-impervious backing sheet, an improved adhesive tab having a fixed end secured to said backing sheet on said outside surface of the diaper and at a marginal location thereof, and a means for providing a shielding and gripping portion including a free end longer than the fixed end and provided with a tacky surface facing in the same direction as said inside surface, and a cover strip provided with a release coating on one surface thereof, releasably attached to, and covering said tacky surface from its outer end toward said marginal location;

said cover strip extending free of and longitudinally beyond said tacky surface to provide a grip tab means; said free end together with said cover strip forming a creasable laminate; and said laminate being folded back over said fixed end and being further folded over on itself.

2. The combination in accordance with claim 1 wherein the adhesive tab is folded in an S-fold, and wherein the cover strip extends beyond said tacky surface towards said fixed end of the tab and is folded back over the distal portion of said free end.

3. The combination in accordance with claim 1 wherein the adhesive tab is folded in a collapsed spiral configuration, and wherein the cover strip extends beyond said tacky surface towards said fixed end of the tab and is folded back on itself.

* * * * *